(12) United States Patent
Shinton et al.

(10) Patent No.: US 12,414,221 B2
(45) Date of Patent: Sep. 9, 2025

(54) RF SOURCE PROTECTION

(71) Applicant: Elekta Limited, Crawley (GB)

(72) Inventors: Ian Shinton, Crawley (GB); Peter Doherty, Crawley (GB); Emma Wooldridge, Crawley (GB)

(73) Assignee: Elekta Limited, Crawley (GB)

( * ) Notice: Subject to any disclaimer, the term of this patent is extended or adjusted under 35 U.S.C. 154(b) by 234 days.

(21) Appl. No.: 18/247,992

(22) PCT Filed: Oct. 8, 2021

(86) PCT No.: PCT/EP2021/077871
§ 371 (c)(1),
(2) Date: Apr. 5, 2023

(87) PCT Pub. No.: WO2022/074199
PCT Pub. Date: Apr. 14, 2022

(65) Prior Publication Data
US 2023/0380049 A1 Nov. 23, 2023

(30) Foreign Application Priority Data
Oct. 9, 2020 (GB) .................................. 2016095

(51) Int. Cl.
*H05H 9/02* (2006.01)
*H01J 23/207* (2006.01)
*H01J 25/54* (2006.01)

(52) U.S. Cl.
CPC ............. *H05H 9/02* (2013.01); *H01J 23/207* (2013.01); *H01J 25/54* (2013.01); *H05H 2277/11* (2013.01)

(58) Field of Classification Search
CPC ............... H01P 3/00; H01L 2924/1421; H01L 2223/6627; H05H 9/02; H05H 2277/11;
(Continued)

(56) References Cited

U.S. PATENT DOCUMENTS

| 3,805,193 A | 4/1974 | Mohr |
| 4,096,457 A | 6/1978 | Snyder |

(Continued)

FOREIGN PATENT DOCUMENTS

| CN | 108696982 A | 10/2018 |
| CN | 208939123 U | 6/2019 |

(Continued)

OTHER PUBLICATIONS

"International Application Serial No. PCT/EP2021/077871, International Search Report dated Jan. 25, 2022", (Jan. 25, 2022), 4 pgs.
(Continued)

*Primary Examiner* — Monica C King
(74) *Attorney, Agent, or Firm* — Schwegman Lundberg & Woessner, P.A.

(57) ABSTRACT

A method of determining a design of a transmission waveguide, the method comprising: providing a system comprising a transmission waveguide connected at a first end thereof to an RF source; generating an electromagnetic field in the system by application of RF energy of a harmonic frequency of the RF source to the transmission waveguide; determining whether a reference location in the RF source meets a requirement relating directly or indirectly to an electromagnetic field in the RF source; and if the requirement is met, outputting the current design of the transmission waveguide as its design.

31 Claims, 9 Drawing Sheets

(58) Field of Classification Search
CPC .... H05H 2007/041; H05H 9/048; H05H 1/46; H05H 7/04; H05H 7/18; H05H 9/00; H05H 2242/20; H05H 2007/048; H05H 2007/122; H05H 7/001; H05H 7/12; H05H 9/044; H05H 9/045; H05H 1/466; H05H 2245/32; H05H 2007/027; H05H 2007/046; H05H 9/04; H05H 1/16; H05H 1/18; H05H 1/54; H05H 7/22; H01J 37/32091; H01J 21/24; H01J 2237/047; H01J 2237/0473; H01J 2237/0475; H01J 2237/063; H01J 3/36; H01J 37/06; H01J 23/30; H01J 25/025; H01J 25/38; H01J 2237/06391; H01J 2237/3321; H01J 2237/3323; H01J 23/04; H01J 23/09; H01J 23/12; H01J 23/24; H01J 23/36; H01J 25/00; H01J 25/04; H01J 25/34; H01J 3/40; H01J 37/32192; H01J 37/32201; H01J 37/3222; H01J 37/32247; H01J 37/32284; H01J 37/32293; H01J 37/32302; H01J 37/3244; H01J 37/32715; H01J 2211/446; H01J 23/075; H01J 23/10; H01J 23/20; H01J 23/207; H01J 23/34; H01J 2329/869; H01J 2329/89; H01J 25/54; H01J 25/68; H01J 25/76; H01J 29/89; H01J 37/32; H01J 5/16; H05B 6/705; H05B 6/72; H05B 6/645; H05B 6/688; H05B 6/6402; H05B 6/6435; H05B 6/6447; H05B 6/6455; H05B 6/687; H05B 6/808; H05B 6/686; H05B 6/70; H05B 6/80; H05B 6/06; H05B 2214/03; H05B 2206/046; H05B 2206/045; H05B 6/6411; H05B 6/6458; H05B 6/6464; H05B 6/6479; H05B 6/66; H05B 6/763; H05B 6/704; H05B 6/74; H05B 2213/06; H05B 6/062; H05B 6/1236; H05B 6/701; H05B 6/702; H05B 6/802; H05B 6/806

See application file for complete search history.

(56) References Cited

U.S. PATENT DOCUMENTS

| | | | | |
|---|---|---|---|---|
| 4,145,692 | A | * | 3/1979 | Armstrong ............ G01S 7/4052 |
| | | | | 342/173 |
| 5,113,160 | A | | 5/1992 | Campisi |
| 5,939,953 | A | | 8/1999 | Yogo et al. |
| 8,674,630 | B1 | | 3/2014 | Cornelius |

FOREIGN PATENT DOCUMENTS

| | | | | |
|---|---|---|---|---|
| GB | 2599720 | A | * 4/2022 | ............. H01J 23/20 |
| JP | 07326500 | A | 12/1995 | |
| JP | 2869000 | B2 | 3/1999 | |
| JP | 2015050491 | A | 3/2015 | |

OTHER PUBLICATIONS

"International Application Serial No. PCT/EP2021/077871, Written Opinion dated Jan. 25, 2022", (Jan. 25, 2022), 9 pgs.

"United Kingdom Application Serial No. 2016095.8, Examination Report dated Apr. 6, 2021", (Apr. 6, 2021), 8 pgs.

"European Application No. 21790157.8, Communication pursuant to Article 94(3) EPC dated Apr. 9, 2025", (Apr. 9, 2025), 12 pgs.

* cited by examiner

RF SOURCE PROTECTION

PRIORITY APPLICATIONS

This application is a U.S. National Stage Filing under 35 U.S.C. § 371 from International Application No. PCT/EP2021/077871, filed on Oct. 8, 2021, and published as WO2022/074199 on Apr. 14, 2022, which claims the benefit of priority to British Application No. 2016095.8, filed on Oct. 9, 2020; the benefit of priority of each of which is hereby claimed herein, and which applications and publication are hereby incorporated herein by reference in their entirety.

FIELD

This disclosure relates to apparatus, devices, systems, computer readable media, and approaches for radiotherapy, and in particular but without limitation to a modified transmission waveguide for prolonging the lifetime of an RF source in a linac system. The disclosure also relates to methods for design and manufacture of a transmission waveguide.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device typically comprises a gantry which supports a beam generation system, or other source of radiation, which is rotatable around a patient. The beam generation system is typically based on a particle accelerator such as a linear accelerator. Linear accelerators (especially those for medical use) accelerate charged particles such as electrons to relativistic speeds along an acceleration path through an accelerating waveguide. The accelerating waveguide has a number of resonant cavities located along the acceleration path. A radiofrequency (RF) electromagnetic wave is applied to the accelerating waveguide which provides an oscillating electric field in each cavity. The field accelerates electrons. The RF energy applied to the waveguide is thus used to accelerate the electrons along the acceleration path. The accelerated electrons can hit a target, for example of tungsten, to generate X-rays for therapy, or can be used directly for imaging or treatment.

A cavity magnetron is a device typically used to create the RF wave. It does this by having a rotating stream of electrons generated from a central cathode (typically by thermionic means) that pass a series of radial cavities spaced around the circumference of the magnetron. As the electrons pass the cavities, they generate RF waves at a frequency determined by the cavity geometry. Due to the geometry of the cavities there are higher and lower operational modes that can be excited, however a magnetron is typically run in a medical linac device using a single designed frequency to which a maximum power is extracted from the magnetron. The RF wave is emitted from the RF window of the magnetron, which is an aperture through which RF waves generated in the magnetron pass when exiting the magnetron.

The magnetron is connected to the accelerating waveguide by means of a transmission waveguide. The transmission waveguide is a waveguide which connects the RF window of the magnetron with an RF window of the accelerating waveguide.

It is important that the magnetron is correctly impedance matched to the system in which it operates in order to prevent or reduce back reflections of the fundamental mode of the magnetron. Even in a well-matched system, back reflections of the fundamental mode can still occur. To address this problem, a circulator or an isolator is usually placed between the magnetron and the accelerating waveguide (usually 'in line' in the transmission waveguide) to prevent too much mismatched RF power being reflected back to the magnetron. In spite of these measures, magnetron lifetimes in linac systems are often shorter than expected.

The present invention seeks to address these, and other disadvantages encountered in the prior art.

SUMMARY

An invention is set out in the independent claims. Optional features are set out in the dependent claims.

BRIEF DESCRIPTION OF THE DRAWINGS

Embodiments will now be described, by way of example, with reference to the drawings of which.

OVERVIEW

In overview, the inventors have recognised that the magnetron lifetime is shortened due to the magnetron absorbing reflected electromagnetic radiation from the accelerator or other harmonic components of the RF system that can be related to a harmonic frequency of the magnetron. This absorbed radiation causes overheating of the cathode and/or anode, which damages these components over repeated cycles of use. The inventors have recognised that of the harmonic frequencies, the second harmonic frequency of the magnetron is most problematic.

Thus, the inventors have recognised that, in addition to mitigating the risk of back-reflected electromagnetic radiation of the fundamental frequency of the magnetron, it is also desirable to mitigate the risk of electromagnetic radiation of a harmonic frequency of the magnetron (preferably the second harmonic) from entering the magnetron. The inventors have also recognised that this problem also exists for other RF sources such as klystrons.

The inventors have devised solutions to this previously unknown problem which include altering the transmission waveguide between the accelerating waveguide and the RF source in order to divert or absorb radiation of the harmonic frequency or to reduce its absorption in the RF source.

The solutions include means for moving maxima of the harmonic frequency away from critical components of the magnetron by altering the design (e.g. the length) of the transmission waveguide, and/or means for absorbing or diverting waves of the harmonic frequency in the transmission waveguide before they reach the RF source.

DETAILED DESCRIPTION

In the following description, reference is made to the accompanying drawings, which form a part hereof, and in which show by way of illustration specific embodiments in which the invention may be practiced. It is to be understood that other embodiments may be utilised, and structural or logical changes may be made without departing from the scope of the present invention. The following description, therefore, is not to be taken in a limiting sense. It is to be understood that, unless specifically noted otherwise, this disclosure provides that any feature or features of the various example embodiments described herein may be combined, in part or whole, with any other such feature or features and that such combination may occur in the absence of any further such feature or features.

The present disclosure relates to a machine, apparatus or device for radiotherapy. The device may be suitable for delivering a beam of radiation to a patient in order to treat a tumour. An example of a system, or sub-system, for generating a beam of radiation is a linear accelerator (linac). Clinical linac devices are configured to deliver high energy radiation to a patient.

Figure 1:
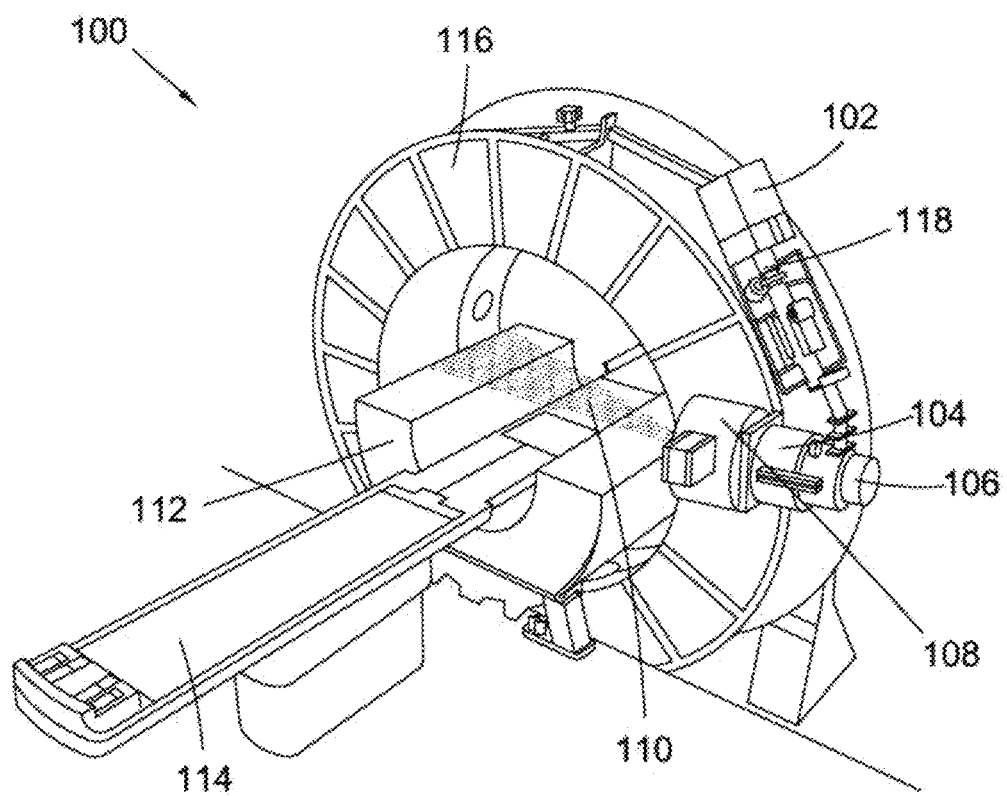
FIG. 1 shows a radiotherapy device or apparatus.

FIG. 1 shows a radiotherapy device. The device and its constituent components will be described generally for the purpose of providing useful accompanying information for the present disclosure. The device shown in FIG. 1 is in accordance with the present disclosure and is suitable for use with the disclosed apparatuses, devices, systems, computer readable media, and approaches for radiotherapy.

The device in FIG. 1 is a system that combines magnetic resonance (M R) imaging capability with a linac-based radiotherapy capability, known as an MR-linac device. Although the device 100 comprises MR imaging apparatus and radiotherapy (RT) apparatus, with the RT apparatus comprising a linac, the present disclosure may be implemented in any radiotherapy device, for example, a linac-based radiotherapy device without magnetic resonance imaging capability. In operation, the MR scanner produces MR images of the patient, and the RT apparatus produces and shapes a beam of radiation and directs it toward a target region within a patient's body in accordance with a radiotherapy treatment plan.

The MR-linac device 100 shown in FIG. 1 comprises a source 102 of radiofrequency waves, transmission waveguide 103, an accelerating waveguide, a source of electrons, a treatment head 104 including a collimator 108 such as a multi-leaf collimator used to shape a treatment beam 110, MR imaging apparatus 112 (shown partially cut away), and a patient support surface 114. The depicted device does not have the usual 'housing' which would cover the MR imaging apparatus and RT apparatus in a commercial setting such as a hospital. In use, the device would also comprise the housing, part of which, together with a ring-shaped rotatable gantry 116, defines a bore. In particular, a part of the housing encloses the inner surface of the ring-shaped gantry, defining a bore through the device 100. The patient support surface 114 is moveable and can be used to support a patient and move them, or another subject, into the bore when an MR scan and/or when radiotherapy is to commence.

The MR imaging apparatus 112 is configured to obtain images of a subject positioned, i.e. located, on the patient support surface 114. The MR imaging apparatus 112 may also be referred to as the MR imager. The MR imaging apparatus 112 may be a conventional MR imaging apparatus operating in a known manner to obtain MR data, for example MR images. The skilled person will appreciate that such a MR imaging apparatus 112 may comprise a primary magnet, one or more gradient coils, one or more receive coils, and an RF pulse applicator.

The RT apparatus comprises a linac-based system or sub-system, which may also be referred to as a radiation source or a beam generation system, or sub-system. The beam generation system is shown in more detail in FIG. 2. The accelerating portion of a linac, in this example the accelerating waveguide, is commonly implemented using a disk-loaded waveguide.

The beam generation system is configured to produce a beam of ionising radiation, otherwise known as the treatment beam 110, that is collimated and shaped by the collimator 108 and directed towards the bore. Typically, a radiation detector is positioned diametrically opposed to the collimator. The radiation detector is suitable for, and configured to, produce radiation intensity data. In particular, the radiation detector is positioned and configured to detect the intensity of radiation which has passed through the subject. The radiation detector may also be described as radiation detecting means and may form part of a portal imaging system.

The beam generation system is attached to the rotatable gantry 116 so as to rotate with the gantry 116. In this way, the beam generation system is rotatable around the patient so that the treatment beam 110 can be applied from different angles around the gantry 116. In a preferred implementation, the gantry is continuously rotatable. In other words, the gantry can be rotated by 360 degrees around the patient, and in fact may continue to be rotated past 360 degrees. The gantry may be ring-shaped. In other words, the gantry may be a ring gantry.

Figure 2:
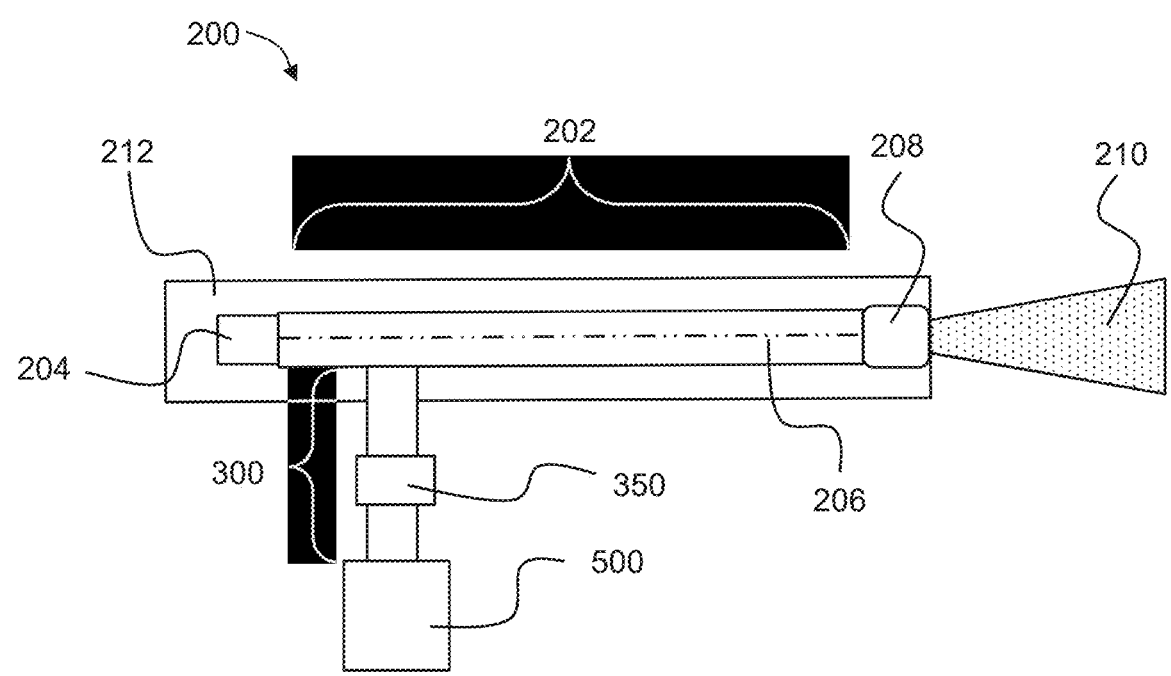
FIG. 2 shows a beam generation system for a radiotherapy device.

The device 100 of FIG. 1 may be controlled by a controller. The controller is a computer, processor, or other processing apparatus. The controller may be formed by several discrete processors; for example, the controller may comprise an MR imaging apparatus processor, which controls the MR imaging apparatus 112; a linac apparatus processor, which controls the operation of the beam generation system; and a subject support surface processor which controls the operation and actuation of the patient support surface 114. The controller is communicatively coupled to a memory, e.g. a computer readable medium. FIG. 2 shows an example linac apparatus that will be described generally for the purpose of providing useful accompanying information for the present disclosure. In particular, the linac apparatus of FIG. 2 is suitable for use as the beam generation system of the device 100 of FIG. 1.

The Linac Apparatus

The linac apparatus 200 comprises an accelerating waveguide 202 and a source 204 of electrons. The source 204 of electrons may be an electron gun, which itself may be either a triode electron gun or diode electron gun.

The accelerating waveguide 202 is configured to accelerate particles, in this case electrons, along an acceleration path 206 into a target 208, in order to produce a treatment beam 210. The accelerating waveguide comprises a series of cells. In this example, each cell has substantially the same shape and dimensions, but in other examples, that may not be so. The cells may be arranged such that each cell is independent, and in that case each cell functions as a separate cavity within which RF energy may resonate or, in other words, each cell is a resonant cavity. In other implementations, such as the example of FIG. 2, the cells may be coupled together and, in that case, the overall coupled structure may be considered to be a single resonant cavity. In such an implementation, although the coupled cells function as a single resonant cavity, individual cells may still be referred to as cavities by those skilled in the art. The acceleration path 206 is coincident with the centre axis of the accelerating waveguide 202. The accelerating waveguide 202, the source 204 of electrons, and the target 208 are enclosed within an evacuated and vacuum-sealed casing 212. As the electrons are accelerated in the accelerating waveguide 202, the electron beam path may be controlled by a suitable arrangement of steering magnets, or steering coils, which surround the accelerating waveguide 202. The arrangement of steering magnets may comprise, for example, two sets of quadrupole magnets.

To ensure that propagation of the electrons is not impeded as they travel toward the target 208, the vacuum-sealed casing 212 is evacuated using a vacuum system to ultra-high vacuum (UHV) conditions. Electrons from the source 204 of electrons can be accelerated to speeds approaching the speed of light in the evacuated accelerating waveguide 202. The evacuation may be performed at the point of manufacture, in which case it is permanently sealed. Alternatively, the evacuation may be performed at the point of device installation, in which case the vacuum may be created and maintained using pumps attached to the linac apparatus 200. The pump system is capable of producing UHV conditions.

A source 500 of radiofrequency waves, such as a magnetron, is configured to produce radiofrequency waves. The source 500 of radiofrequency waves is coupled to the accelerating waveguide 202 via a transmission waveguide 300 comprising a circulator 350 and is configured to pulse radiofrequency waves into the accelerating waveguide 202. Typically, the radiofrequency waves are input into a particular cell of the accelerating waveguide 202. Radiofrequency waves may pass from the source 500 of radiofrequency waves through an RF output window of the magnetron designed to maintain UHV but pass RF and into the transmission waveguide 300. The transmission waveguide 300 is coupled with the accelerating waveguide 202 and joins the accelerating waveguide 202 at a substantially 90° angle as is shown for the transmission waveguide 300 in FIG. 2. The transmission waveguide 300 may join the accelerating waveguide 202 via a so-called 'elbow joint' or 't-shaped joint'. The circulator 350 prevents the RF waves of the fundamental frequency of the magnetron from traveling back to the source 500 of radiofrequency waves. The transmission waveguide 300 may also be described as a transport waveguide.

A source of radiofrequency waves can be used to operate a linac with either a standing wave or a traveling wave configuration. In a standing wave configuration, the source 500 of radiofrequency waves is configured to pulse RF waves into the accelerating waveguide 202, in order to set up a standing wave of varying electric field that is suitable for accelerating charged particles. The RF waves may be referred to as oscillating, or an oscillating electric field, and may also be described using the related terms RF energy, RF power, or RF voltage, where each physical property relates to the corresponding property of the RF wave.

An example RF wave frequency as the fundamental or operating frequency of the magnetron is 3 GHz. The source 500 of radiofrequency waves may be a commercially available magnetron such as an E2V 3.1 MW magnetron operating at 3 GHz, or any standard radiotherapy magnetron. The pulse frequency of the source 500 of radiofrequency waves is typically much lower than the RF wave frequency. Typically, the source 500 of radiofrequency waves produces each pulse with a particular phase in order to improve the stability of the standing wave within the accelerating waveguide 202. After it has been pulsed into the accelerating waveguide 202, the RF energy dissipates into the walls of the accelerating waveguide 202, is directed to a beam dump or reflects back along the accelerating waveguide 202 to set up a standing wave inside the accelerating waveguide 202.

The source 204 of electrons, such as an electron gun, is also coupled to the accelerating waveguide 202 and is configured to inject electrons into the accelerating waveguide 202. The injection of electrons into the accelerating waveguide 202 is synchronised with the pulsing of the radiofrequency waves into the accelerating waveguide 202.

In some implementations, a portion of an accelerating waveguide in a linac may be referred to as a buncher. The buncher may comprise one or more cells of the accelerating waveguide. Within the buncher, the phase of the RF wave, whether a standing wave or traveling wave, slows down some electrons to allow other electrons time to catch up. In particular, the electrons may be injected by the source 204 of electrons at a point that is not centred on the peak of the RF wave. The electrons are then free to move together in so called "packets" or "bunches" and the bunches quickly accelerate to relativistic speeds through the subsequent cells of the accelerating waveguide. The accelerating waveguide may be designed with a buncher that is optimised to produce an electron beam with a particular energy and intensity by bunching electrons into a beam of short pulses.

RF waves may be input to the accelerating waveguide at a particular cell, or at more than one cell. In particular, RF waves may be input at a cell that is adjacent to the buncher portion of the accelerating waveguide. In the example of FIG. 2, the first two cells on the left hand side of the accelerating waveguide 202 are the buncher and the following cells act to accelerate the electrons to relativistic speeds. Alternatively, the RF waves may be input into one or more of the cells belonging to the buncher section of the accelerating waveguide 202.

Once the electrons have been accelerated, they may pass into a flight tube. The flight tube is connected to the accelerating waveguide by a connecting tube. The flight tube is also kept under vacuum conditions. This connecting tube or connecting structure is termed a drift tube. The drift tube also forms part of a vacuum tube along with the other components within the vacuum-sealed casing 212. The electrons may travel along a slalom path toward the heavy metal target. Whilst the electrons travel through the flight tube, an arrangement of focusing magnets act to direct and focus the beam on the target. The slalom path allows the overall length of the linac to be reduced while ensuring that the beam of accelerated electrons, which is comprised of electrons with a small spread of energies, is focused on the target.

The design and operation of the source 500 of radiofrequency waves, source 204 of electrons and the accelerating waveguide 202 is such that the radiofrequency waves accelerate the electrons to very high energies as the electrons propagate through the accelerating waveguide 202 along the acceleration path 206. To alter the energy of the electron beam, the input power radio frequency (RF) delivered to the accelerating waveguide must be increased so that the electrons are accelerated to faster energies, such as 8 MeV or 10 MeV.

The electrons travel toward the target 208 which may comprise, for example, tungsten, or another heavy metal. The impact of the electrons on the target 208 produces x-rays which form the treatment beam 210. When the electrons strike the target 208, x-rays are produced in a variety of directions. A primary collimator may block x-rays travelling in certain directions and pass only forward travelling x-rays to produce the treatment beam 210. The x-rays may be filtered and may pass through one or more ion chambers for dose measuring. The beam can be shaped in various ways by beam-shaping apparatus, for example by using the multi-leaf collimator 108, before it passes into the patient as part of radiotherapy treatment.

If a flight tube is used, the target is located inside the flight tube and is located at the end of the flight tube to seal the vacuum system. The flight tube also comprises a target window, which is transparent to x-rays, which is positioned to allow the x-rays which are produced when the linac apparatus is in operation to pass from the evacuated flight tube through the target window and into the treatment head.

In some implementations, the electrons are accelerated within an accelerating waveguide by using a travelling wave rather than a standing wave. The accelerating waveguide 202 will allow traveling waves of particular frequencies to propagate. The accelerating waveguide 202 must be designed such that the phase velocity of the traveling wave does not exceed the speed of light, otherwise no acceleration of electrons will occur. For example, a disk-loaded waveguide design may be used.

For an accelerator that uses a traveling wave, in addition to an RF input, the accelerating waveguide will have an RF output configured to transfer RF energy out of the accelerating waveguide and prevent it from reflecting and establishing a standing wave. If a drift tube is used adjacent to the accelerating waveguide, the RF output may be coupled to the drift tube. As with the transmission waveguide which introduces RF power to the accelerating waveguide, the pipe or tube through which RF power exits the waveguide connects to the accelerating waveguide via an elbow joint or 'T-shaped' joint. RF waves pass out from the evacuated system via an RF output window which seals the vacuum system.

Further Variations in Beam Generation System Design

Referring to the apparatus of FIG. 2, variations in design and components are possible or desirable depending upon the application requirements. For example, requirements may vary depending upon the desired type and energy of the treatment beam or depending upon the mechanical or structural design of the overall device in which the apparatus is to be used, such as the device 100 of FIG. 1.

In some implementations, the source 500 of radiofrequency waves may be a klystron, rather than a magnetron. Similarly, in some implementations, the source 500 of radiofrequency waves may be operated continuously rather than in a pulsed manner.

In some implementations, the linac apparatus 200 is configured to emit either an x-ray beam or an electron particle beam. Such implementations allow the device to provide electron beam therapy, i.e. a type of external beam therapy where electrons, rather than x-rays, are directed toward the target region as the therapeutic radiation. It is possible to 'swap' between a first mode in which x-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window may be made of nickel. The electron window is substantially or partially transparent to electrons and allows electrons to exit the linac apparatus 200.

The linac apparatus 200 also comprises several other components and systems as will be understood by the skilled person. For example, in order to ensure the linac does not leak radiation, appropriate shielding is also provided. The whole system is cooled by a water cooling system (not shown in the figures). The water cooling system may be used, in particular, to cool the acceleration waveguide 202, the target 208, and the source 500 of radiofrequency waves.

Example of a Standard Transmission Waveguide

Figure 3:
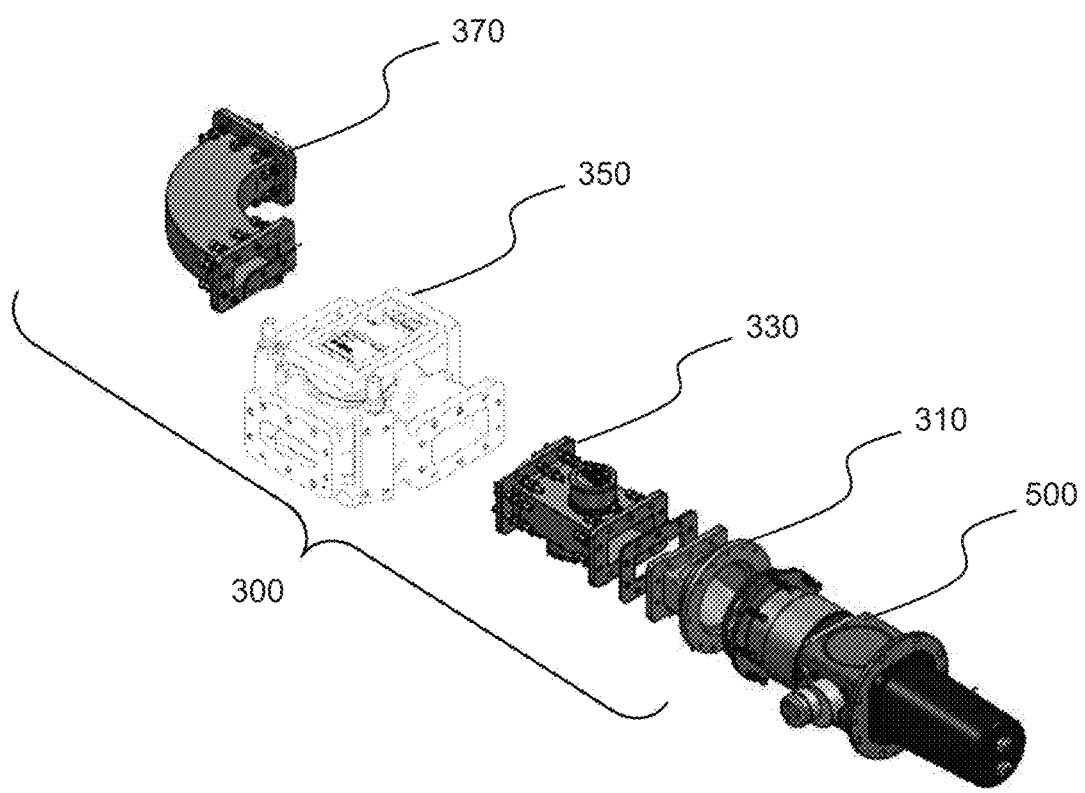
FIG. 3 shows an exploded isometric view of a magnetron and transmission waveguide according to the prior art.

FIG. 3 shows an isometric view of a transmission waveguide 300 according to the prior art and an RF source 500 connected thereto.

The RF source 500 may be a magnetron (e.g. a cavity magnetron or magnetron tube) or a klystron.

The RF source 500 in FIG. 3 includes an output RF window comprising a circular aperture. The output RF window is surrounded by an annular flange.

The transmission waveguide of FIG. 3 includes an adaptor 310, a first waveguide section 330, a circulator 350, and a second waveguide section 370.

This transmission waveguide can be used in a linear accelerator as shown in FIG. 2, but also could be used in other accelerators (e.g. a curved accelerator such as a cyclotron or a synchrotron). The below examples and discussion related to the acceleration of electrons, but the waveguide can be used in the acceleration of any charged particle and therefore in any charged particle accelerator. For example, protons, positrons and ions can be accelerated using the techniques described herein.

The transmission waveguide may couple the RF power into the accelerator via an 'in line' arrangement. Alternatively, the transmission waveguide may include one or more E- and/or or H-bend waveguide sections and, optionally, a power coupler section to transition the power into the accelerating waveguide.

The adaptor 310 includes a tubular arrangement having a circular aperture at one end thereof and a rectangular aperture at the other end. The tubular arrangement tapers smoothly between the two apertures. The circular aperture is surrounded by an annular flange arranged to mate with the annular flange surrounding the output RF window of the magnetron. The rectangular aperture of the adaptor is surrounded by a rectangular flange.

Although, the adaptor 310 is shown as having a circular aperture at one end and a rectangular aperture at the other, other types of adaptor may be used. The function of the adaptor is to taper smoothly between the shape of the RF window of the magnetron and the cross-sectional shape of the first waveguide section. Therefore, if the either the RF window of the magnetron or the cross-sectional shape of the first waveguide section are different from those shown in FIG. 3, the adaptor will accordingly have differently shaped apertures.

The first waveguide section 330 includes a tubular arrangement having a rectangular aperture at each end and a cross-section which does not vary in shape or dimensions from one aperture to the other. Each aperture has the same shape and dimensions as the rectangular aperture of the adaptor 310 and is surrounded by a flange. The flange surrounding the aperture at a first end of the first waveguide section 330 is arranged to mate with the flange surrounding the rectangular aperture of the adaptor 310.

The circulator 350 is tuned to the fundamental RF frequency of the magnetron. The circulator is arranged to allow passage of RF waves of the fundamental frequency of the magnetron travelling from the magnetron to the accelerating waveguide and divert RF waves of the same frequency travelling through the circulator in the opposite direction so that they do not reach the magnetron.

The circulator 350 has a first, second and third port comprising first, second and third apertures, respectively. Each of the apertures is rectangular in shape and is surrounded by a flange. The flange surrounding the first aperture is arranged to mate with the flange surrounding the aperture at the second end of the first waveguide section. The second aperture is at an opposite end of the circulator to the first aperture and the third aperture is in a side or face of the circulator which extends between the ends having the first and second apertures.

Waveguide paths internal to the circulator connect the first to third apertures as follows. A first waveguide path extends between the first and second apertures, a second waveguide path extends between the second and third apertures and a third waveguide path extends between the third and first apertures. The internal configuration of the circulator 350 is such that RF waves having the fundamental frequency of the magnetron are allowed to travel: (i) from the first to the second aperture (but not in the reverse direction), (ii) from the second to the third aperture (but not in the reverse direction), and (iii) from the third to the first direction (but not in the reverse direction).

An S-matrix (or scattering matrix) defining an idealised three-port circulator as described in words above is as follows:

$$S = \begin{vmatrix} 0 & 0 & 1 \\ 1 & 0 & 0 \\ 0 & 1 & 0 \end{vmatrix}$$

The third aperture may be connected, either directly or via another waveguide, to a beam dump or other RF load arranged to absorb RF waves, in particular RF waves of the fundamental mode reflected back from the accelerating waveguide towards the magnetron.

In some embodiments, the circulator 350 may be a four-port circulator. In this arrangement, in addition to the first to third ports, the circulator also includes a fourth port. Though there are differences in their construction, the three and four-port circulators effectively both serve the same purpose. A four port circulator is more complicated as it is formed by combining two magic T junctions together with a fixed 180 deg phase shifter to give the following idealised scattering matrix:

$$s = \begin{bmatrix} 0 & 0 & 0 & 1 \\ 1 & 0 & 0 & 0 \\ 0 & 1 & 0 & 0 \\ 0 & 0 & 1 & 0 \end{bmatrix}$$

Which can be described in words as transmission from port 1 to 4, transmission from port 2 to 1, transmission from port 3 to 2 and transmission from port 4 to 3. The RF source is connected to port 1, waveguide section connection to the acceleration waveguide is connected to port 4. A low power load is connected to port 3 and high power load is connected to port 2.

It is easier to produce a well-matched system using a four-port circulator as the system can be impedance matched more easily using the loads connected to ports 2 and 3. Four port circulators have traditionally been considered more stable than three-port circulators when used in in a medical linac environment where there are large changes in RF due to thermal effects, arcing etc.

The second waveguide section 370 is similar in structure to the first waveguide section 330. The second waveguide section 370 includes a tubular arrangement having a rectangular aperture at each end and a cross-section which does not vary in shape or dimensions from one aperture to the other.

Each aperture has the same shape and dimensions as the second aperture of the circulator and is surrounded by a flange. The flange surrounding the aperture at a first end of the second waveguide section is arranged to mate with the flange surrounding the second aperture of the circulator. The flange surrounding the aperture at the second end of the second waveguide is arranged to mate with a corresponding flange around the RF window of the accelerating waveguide.

By way of an example, a typical specification for a suitable first and/or second waveguide section is WG10 (also known as EIA Standard WR284 or IEC Standard R32). A waveguide of this type has a recommended operating frequency of 2.60 to 3.95 GHz, which is suitable for a typical fundamental mode RF wave generated by a magnetron in a linac (typical operating frequency approximately 3 GHz).

The function of the transmission waveguide 300 is to act as a suitable conduit for the lossless transfer of RF waves of the fundamental frequency of the magnetron. Therefore, other shapes, sizes and waveguide specifications can be used which enable this function to a sufficient degree.

Although the arrangement of FIG. 3 shows an adaptor 310 and first waveguide section 330 between the RF window of the RF source 500 and the first aperture of the circulator 350, other components can be used to replace these two components, such as a single adaptor/waveguide section with a more gradual taper than the adaptor 310 in FIG. 3.

Two or more waveguide sections can be used in place of the first waveguide section. Similarly, two or more waveguide sections can be used in place of the second waveguide section. If necessary, a further adaptor may be used between the second waveguide section and the RF window of the accelerating waveguide.

If the RF window of the magnetron is of a suitable shape and size, there need not be an adaptor and the transmission waveguide in its simplest form can simply be a single waveguide section between the RF window of the magnetron and the RF window of the accelerating waveguide.

The various mated flanges are fastened together using bolts or other fixing means to form a seal between the flanges.

In operation (as shown here with a three port circulator), the circulator 350 receives from the magnetron an RF wave of the fundamental frequency of the RF source 500 at the first port. The RF wave travels through the first waveguide path from the first port to the second port. The RF wave then exits the second port and travels onward toward the RF window of the accelerating waveguide 202. An RF wave of the fundamental frequency of the RF source 500 travelling in the opposite direction (i.e. from the accelerating waveguide 202 to the second port of the circulator 350) is received at the second port and is then guided by the second waveguide path from the second port to the third port. The RF wave then exits the third port and travels into (or onward toward) the beam dump.

Thus, the circulator 350 operates to allow an RF wave of the fundamental frequency of the RF source 500 to travel from the RF window of the magnetron through the circulator to the RF window of the accelerating waveguide 202. The circulator 350 does not allow travel of an RF wave of this frequency in the opposite direction from the RF window of the accelerating waveguide 202 to the RF window of the RF source 500. Thus, back-reflected waves having the fundamental frequency are prevented from travelling through the circulator 350 into the RF source 500.

As the circulator is a narrow bandwidth component tuned to frequencies around or close to the fundamental frequency of the magnetron, RF waves of other frequencies may not be affected in the same way as described above for the fundamental frequency. That is, if the frequency of an RF wave is sufficiently different from the fundamental frequency, the circulator will not operate as described above. RF waves received at the first port may still be directed along the first waveguide path to the second port. However, a significant proportion of the energy of RF waves travelling in the opposite direction will travel from the second port through the circulator to the first port and onward into the magnetron. Therefore, back-reflected waves, or waves generated in other parts of the linac, having a frequency other than the fundamental frequency of the magnetron may travel through the circulator 350 toward the RF source 500.

Problems with Prior Art Systems

In a linac radiotherapy machine, typical magnetron lifetimes are expected in the order of about 5000 high tension (HT) hours (the time period in which RF power is being supplied by the RF power source in this instance a magnetron), which constitutes a lifetime of about 5 years of typical clinical use. However, the inventors have observed that in reality magnetron lifetimes are considerably shorter, sometimes as much as 10 times shorter. The inventors have also made the following additional observations:

1) When the magnetrons and transmission waveguides of linac machines are connected to a load, rather than the accelerating waveguide (after the circulator), the lifetime of the magnetron is comparatively longer for the same intensity and frequency of use. Therefore, there is an adverse effect on the magnetron lifetime associated with its operation within a linac radiotherapy machine.
2) A high amplitude RF wave of the second harmonic frequency of the magnetron is present in linac systems.
3) The accelerating waveguide has a mode with a large R/Q (i.e. a lot of stored power) that is very close to/or coincides with the second harmonic frequency of the magnetron.
4) As explained above, the typical circulator in the transmission waveguide is designed to operate at the fundamental frequency of the magnetron and is not designed to prevent the passage of RF waves of the second harmonic frequency in the direction from the accelerating waveguide through the circulator to the magnetron.
5) Experiments carried out by the inventors have shown that by adjusting the path length of the transmission waveguide (from the RF window of the accelerating waveguide to the RF window of the magnetron) the lifespan of the magnetron can be affected (adversely or beneficially) depending on the path length relative to the wavelength of the second harmonic of the magnetron.

The inventors derived from the above observations that the magnetron cathode can be adversely affected by higher order mode (HOM) RF waves including frequencies at the second harmonic frequency of the magnetron travelling into the magnetron through the transmission waveguide. These HOM frequencies are being absorbed in the magnetron and converted to heat energy in the cathode, thus degrading the cathode and other components in the magnetron so that the lifespan of the magnetron is reduced.

Figure 4A:
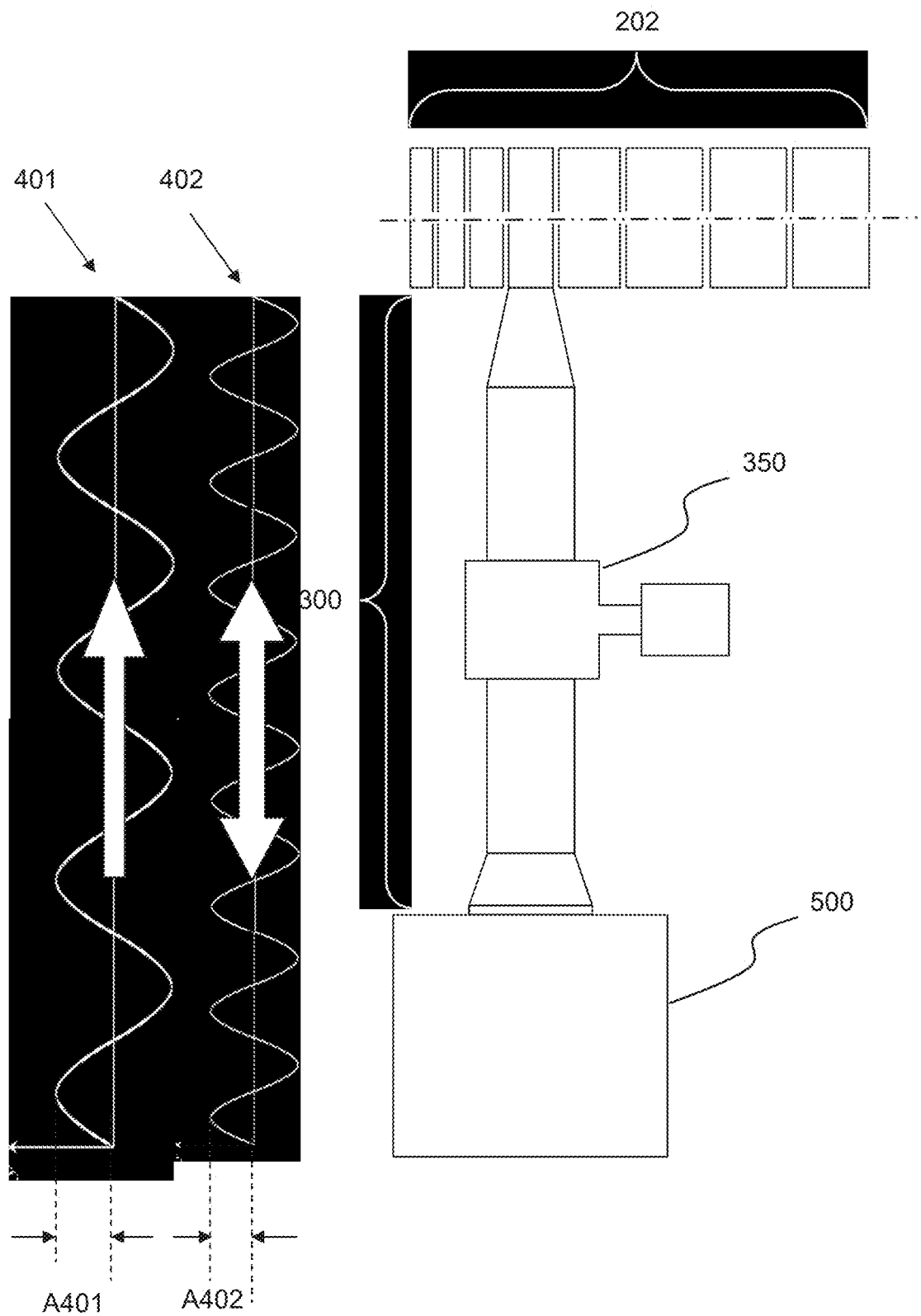
FIG. 4A shows a system including a transmission waveguide connected between a magnetron and an accelerating waveguide in accordance with the prior art, and a schematic of waves of the fundamental and a harmonic frequency of the magnetron in the system.

FIG. 4A shows a system including a transmission waveguide 300 connected between a RF source 500 and an accelerating waveguide 202 in accordance with the prior art, and a schematic of waves of the fundamental 401 and a harmonic 402 frequency of the magnetron in the system. Although shown to one side of the transmission waveguide 300 and the RF source 500 in the figure, the waves 401 and 402 are representative of those travelling in the transmission waveguide 300 and RF source 500.

The presence of the circulator 350 in line in the transmission waveguide 300 has the effect of allowing travel of the fundamental waves 401 in the transmission waveguide 300 in the direction from the RF source 500 to the accelerating waveguide 202, but not in the opposite direction as these are diverted to the port in the side of the circulator shown. However, harmonic waves 402 of the magnetron are allowed to travel in either direction since the circulator 350 is not tuned to perform its function at the harmonic frequency of the RF source 500.

Figure 4B:
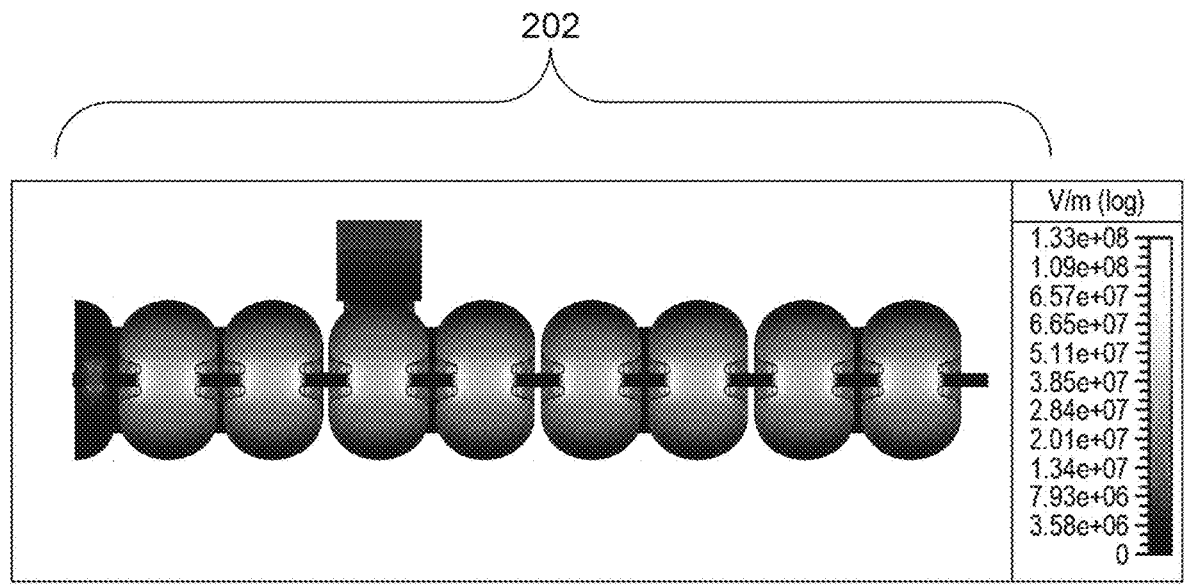
FIGS. 4B and 4C show the electromagnetic field in the accelerating waveguide due to the fundamental and harmonic waves, respectively, in the system of FIG. 4A.

FIG. 4B shows the treatment mode at the end of the accelerating waveguide 202 inside the linac. This treatment mode results from the transmission of the fundamental waves 401 from the RF source 500 through the transmission waveguide into the accelerating waveguide as illustrated in FIG. 4A.

Figure 4C:
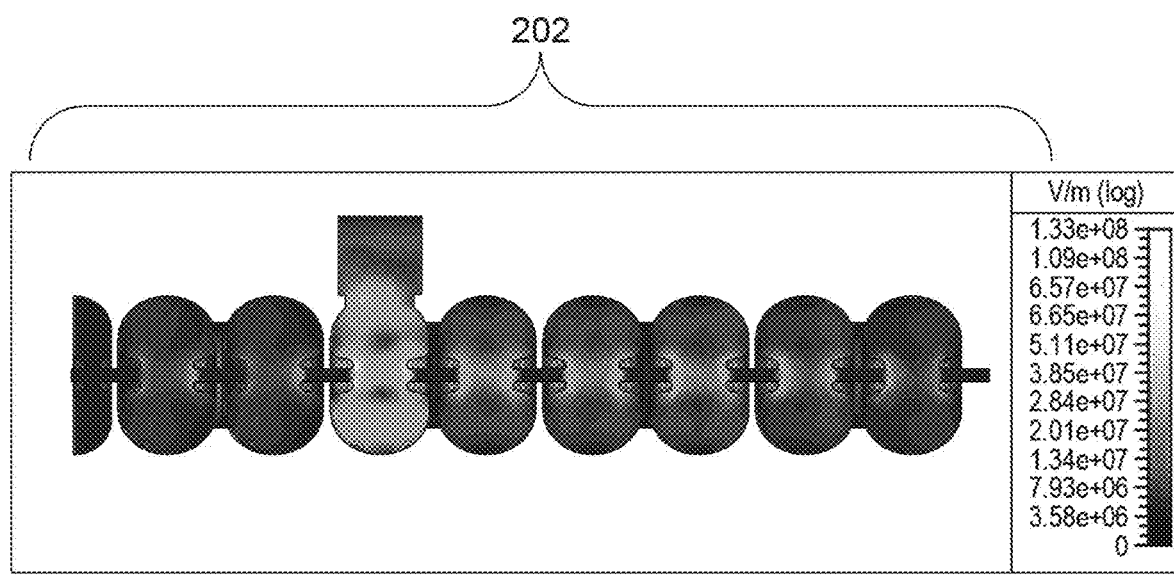

FIG. 4C shows the excitation in the accelerating waveguide 202 by the second harmonic frequency 402 of the magnetron. In this operational mode accelerating waveguide reflects back the harmonic waves 402 through the transmission waveguide 300 into the RF source. This produces a noticeable effect in the RF source because the circulator 350 (see FIG. 4A) does not prevent this reflected mode from entering the RF source 500 as depicted by the reflected form of harmonic waves 402 shown in FIG. 4A.

Transmission Waveguides According to Embodiments

In accordance with embodiments, the transmission waveguide between the magnetron and accelerating waveguide is modified to reduce the amount of radiation of a harmonic (preferably the second harmonic) frequency of the magnetron being absorbed by the magnetron. The described embodiments are modifications of the transmission waveguide 300 shown in FIG. 3 or FIG. 4A. However, the embodiments are not limited to modifications of these particular transmission waveguides and such modifications can be applied to any transmission waveguide configured to guide RF waves of the fundamental frequency of the magnetron.

In some embodiments, the transmission waveguide is modified to absorb radiation of the harmonic frequency. This can be achieved by, for example, adding to the transmission waveguide absorbers or filters designed to pass radiation of the fundamental frequency while absorbing radiation of the harmonic frequency.

Alternatively, or addition, the transmission waveguide is modified so as to allow the normal passage of the energy of the fundamental mode through the transmission waveguide while diverting waves of the harmonic frequencies to prevent their onward travel into the magnetron. An example of this is a broadband isolator added 'in line' in the transmission waveguide that has been designed to discriminate out the unwanted harmonic frequencies.

Alternatively, or in addition, the path length of the transmission waveguide is modified to alter a position of a maxima (or 'hotspot') of the harmonic frequency relative to the magnetron so that the amount of the harmonic frequency absorbed by the magnetron is reduced. This can be achieved by, for example, fixing a path length transmission waveguide (i.e. total length relative to a multiple of the wavelength of the second harmonic of the magnetron) so that a maximum or maxima of the harmonic frequency is moved away from a component of the magnetron, such as the cathode, or in the case of a klystron, the electron gun or other critical component.

Therefore, transmission waveguides according to embodiments are the same as those described with reference to FIG. 3 or 4A are other transmission waveguides suitable for guiding RF waves of the fundamental frequency of the magnetron, but with one or more of the following further features:

An RF attenuator configured to absorb RF waves of a harmonic frequency of the magnetron.
An RF filter configured to filter out RF waves of a harmonic frequency of the magnetron.
An RF divider configured to divert RF waves of a harmonic frequency such as the second harmonic frequency of the magnetron which are travelling in the transmission waveguide. In embodiments, the RF divider can be an RF diverter or an RF reflector. The divider may be a circulator tuned to the harmonic frequency.
An RF spacer or waveguide section dimensioned to move a maxima of an RF wave of the harmonic frequency of the magnetron relative to the cathode or another component of the magnetron.

As described herein, in embodiments the harmonic frequency of the RF source referred to is the second harmonic frequency, but this disclosure is not limited thereto. In addition, in embodiments the RF source is described as a magnetron, however the RF source may be any suitable RF source, for example a klystron. An example of the fundamental frequency of the RF source is 3 GHz. Although this example of an RF source fundamental operating frequency is provided, the fundamental frequency of the RF source described herein can be any frequency suitable for driving the accelerator in the system in question.

Figure 5:
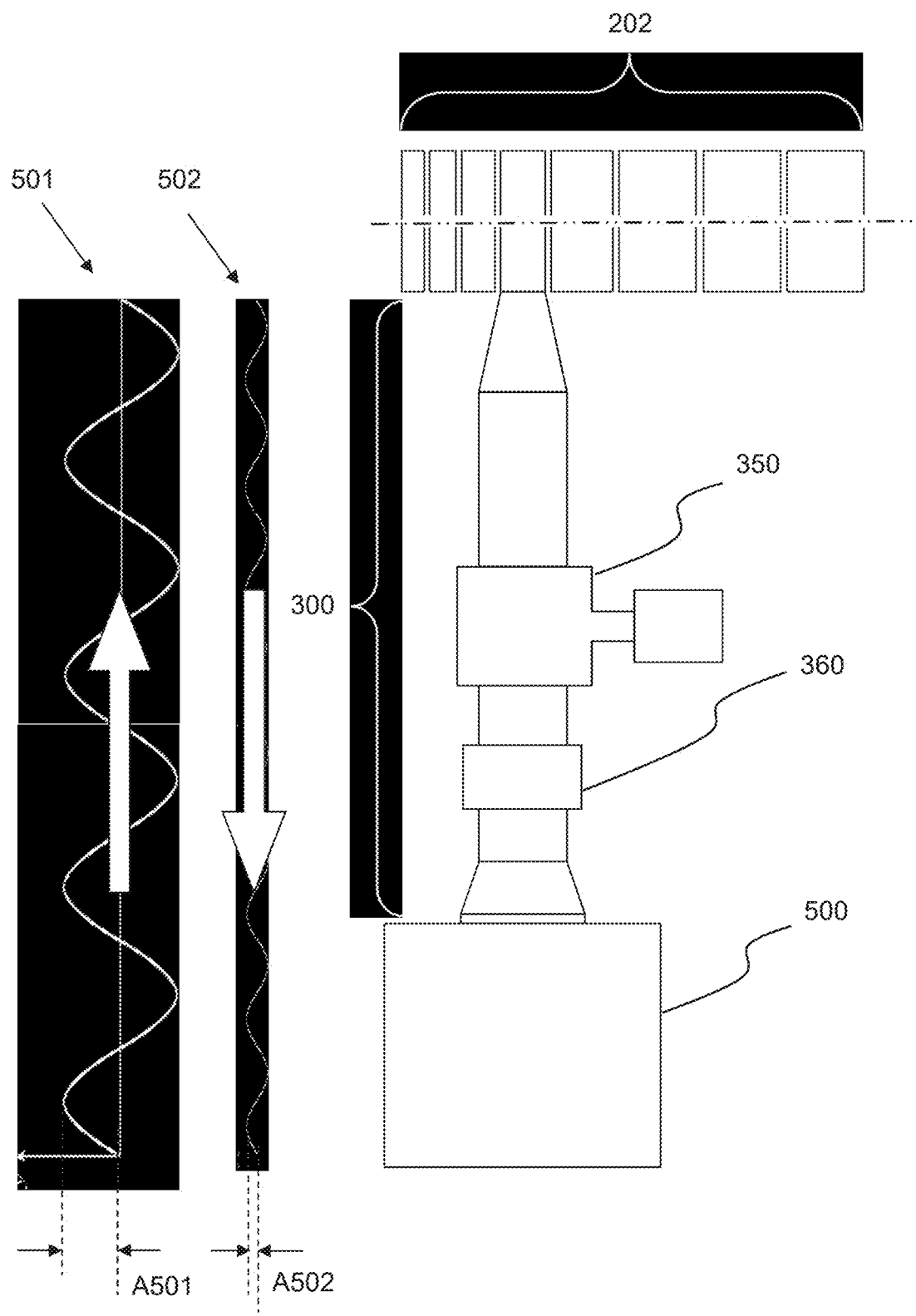
FIG. 5 shows a system including a transmission waveguide connected between a magnetron and an accelerating waveguide in accordance with embodiments, and a schematic of waves of the fundamental and a harmonic frequency of the magnetron in the system.

FIG. 5 shows a system including a transmission waveguide 300 connected between a RF source 500 and an accelerating waveguide 202 in accordance with embodiments, and a schematic of waves of the fundamental frequency 501 and a harmonic frequency 502 of the magnetron in the system. Although shown to one side of the transmission waveguide 300 and the RF source 500 in the figure, the waves 501 and 502 are representative of those travelling in the transmission waveguide 300 and RF source 500.

In contrast with the system shown in FIG. 4A, the transmission waveguide 300 of the system of FIG. 5 includes an RF attenuator 360 configured to dampen (or attenuate) waves of the harmonic frequency 502 of the magnetron. As shown in the wave schematics in FIG. 5, the amplitude A501 of the fundamental frequency 501 is not attenuated (or not attenuated to a significant degree) compared with the corresponding amplitude A401 of the fundamental frequency 401 shown in FIG. 4A. However, due to the presence of the RF attenuator 360, waves of the harmonic frequency 502 travelling in the direction towards the magnetron have a lower amplitude A502 than the corresponding amplitude A402 of waves of the harmonic frequency 402 shown in FIG. 4A.

RF Attenuator

In embodiments, the transmission waveguide includes an RF attenuator configured to attenuate (or dampen) RF waves of the second harmonic frequency of the magnetron. The RF attenuator may be an RF absorber or may be configured to attenuate the RF waves by diverting all or a proportion thereof in the transmission waveguide to prevent them from onward travel toward the magnetron.

The RF attenuator attenuates RF waves of the second harmonic frequency to a greater degree than RF waves of the fundamental frequency of the magnetron. This ensures that the efficacy of the transmission waveguide as a transmitter of RF waves of the fundamental frequency of the magnetron is not affected to an unacceptable degree. Preferably, the RF attenuator dampens RF waves of the second harmonic frequency but does not dampen RF waves of the fundamental frequency of the magnetron.

An RF wave can be represented by equation 1

$$y(x) = Ae^{-\lambda x}(\omega x - \phi) \qquad (1)$$

Where $y(x)$ is the amplitude at distance x; A is the maximum amplitude of the RF wave; $\lambda$ is the decay constant, $\phi$ is the phase angle at x=0, and $\omega$ is the angular frequency.

The RF attenuator is configured to influence the decay constant for waves in the transmission waveguide. The waves may be standing waves set up as the result of interaction of a first travelling wave emitted by the RF source and a second travelling wave reflected back toward the RF source. Alternatively, the waves may be travelling waves either generated by the RF source and reflected back toward the RF source or originating from elsewhere in the system, such as in the accelerating waveguide.

The decay constant can be measured by detecting a first amplitude of a first maxima of the RF wave at a first point in the transmission waveguide a first distance from the RF window of the magnetron; and second amplitude of a second maxima of the RF wave at a second point in the transmission waveguide a second distance from the RF window of the magnetron, wherein the first distance is greater than the second distance. The presence of the RF attenuator increases a decay constant $\lambda_2$ for RF waves of the second harmonic frequency of the magnetron. The presence of the RF attenuator may also increase the decay constant $\lambda_1$ for RF waves of the fundamental frequency of the magnetron, but to a lesser degree than the decay constant $\lambda_2$. However, the ratio $\lambda_1/\lambda_2$ is less than 1 and preferably less than 0.7. However, in some embodiments a frequency dependent RF attenuator is used (e.g. an attenuator designed to attenuate a harmonic frequency of the magnetron, such as the second harmonic frequency, but not the fundamental frequency of the RF source) and its position is therefore less critical. That is, the fundamental frequency of the RF source may be below the cut-off frequency of the RF attenuator.

In embodiments, the RF attenuator comprises an RF waveguide section or an RF cavity, for example a resonator cavity such as a pillbox. The RF attenuator is preferably dielectrically loaded by including an RF absorbing coating on part or whole of the internal surface thereof. If only a part of the internal surface is coated, this may be in the form of a pattern including coated areas with uncoated areas therebetween, for example a series of tiles having spaces therebetween or a grid of coated or uncoated areas. The greater the amount of material in the coating the greater the amount of RF power the RF attenuator can absorb. More material can be included in the coating by increasing the coating thickness. However, the more dielectric material added (or the more area covered by the dielectric material) the more the design of the system may be pulled off frequency. In this case the system may have to be modified to compensate for this, for example with additional parts or geometry.

The material used in the coating can be any material suitable for absorbing RF waves of the second harmonic frequency of the magnetron, for example a ferrite or silicon-carbide based material.

In embodiments, the RF attenuator comprises a waveguide filter, such as a waffle iron filter. A waffle iron filter is a variation of the corrugated-waveguide filter but with longitudinal slots cut through the corrugations resulting in an internal structure that has the appearance of a waffle-iron. The waveguide filter is configured to pass waves of the fundamental frequency of the magnetron while attenuating (or stopping) waves of a harmonic frequency either reflected by the RF system back to the magnetron or stopping the higher order modes generated by the magnetron getting into the RF system to be reflected back.

The RF attenuator can be positioned anywhere in the transmission waveguide. The position of the RF attenuator is defined by the position of its centre (the centre of the absorbing region of the damper). In embodiments, the RF attenuator is placed at a position which corresponds to a function of the RF wavelength that is to be damped.

In embodiments, the position of the RF attenuator is not less than $\lambda$, and preferably not less than $2\lambda$, from the RF window of the magnetron, where $\lambda$ is the wavelength of the fundamental frequency of the magnetron. Preferably, the position of the RF attenuator is between the RF window of the magnetron and before the circulator (if present). Advantageously, this reduces the risk that the second harmonic being produced from the magnetron will enter the rest the linac system. However, in other embodiments the RF attenuator can be placed in any position in the transmission waveguide.

In embodiments, the RF attenuator is positioned where enough coupling can be obtained between the attenuator and the frequency that is to be damped, ideally this is at a maxima of the harmonic rather than a null as this is where the most effective damping of the second harmonic can take place. The position of a maxima of the harmonic frequency is calculated—this will be at:

$$x = \left(n \pm \frac{1}{4}\right)\lambda_2 \tag{2}$$

where n is a natural number and $\lambda_2$ is the wavelength of the harmonic (e.g. second harmonic) frequency of the magnetron; x is the distance from the RF window of the magnetron at which the amplitude of the second harmonic frequency of the magnetron is highest. The nulls in the transmission waveguide would normally be at the magnetron RF window and the RF window of the accelerating waveguide for the fundamental frequency and harmonic frequency.

Another criterion for the RF attenuator is that it must be designed such that it does not adversely affect the fundamental frequency. That is, it is important that the RF attenuator does not dampen RF waves of the fundamental frequency of the magnetron (or that the damping of the fundamental mode is below a threshold damping). Therefore, in embodiments, the resonant versions of the RF attenuator described herein are configured such they have a cut-off frequency, below which no or very little damping occurs, and wherein the fundamental frequency of the magnetron (or RF source) is below the cut-off frequency of the RF attenuator and hence is not affected.

In other embodiments, rather than being an absorber, the RF attenuator is configured to divert RF waves travelling in the transmission waveguide towards the magnetron. The RF waves are diverted to a beam dump or other part of the system or within the RF attenuator itself rather than being allowed to reach the magnetron.

In some embodiments, the RF attenuator is an isolator. The isolator performs like diode in that it allows transmission of RF waves one direction, but prevents transmission of RF waves in the opposite direction through the transmission waveguide. The isolator can be described as a wide band device in that it affects RF waves within a larger frequency range than a circulator. The isolator need not be tuned to the second harmonic frequency of the magnetron and may perform the same function on RF waves of the fundamental and harmonic frequencies of the magnetron, because it is not usually a requirement of the linac system that waves of the fundamental frequency need to be transmitted back to the magnetron. Thus, the isolator may prevent transmission of RF waves of both the fundamental and (second) harmonic frequency from travelling in the transmission waveguide in the direction towards the magnetron and may allow transmission of RF waves of both the fundamental and (second) harmonic frequency in the opposite direction.

The isolator is preferably positioned in line in the transmission waveguide between the RF window of the accelerating waveguide and, if present, the circulator. Advantageously, this prevents RF waves of the harmonic frequency of the magnetron from entering into the circulator and causing damage thereto. In this case, the isolator is configured to pass RF waves of the harmonic frequency travelling from the circulator to the accelerating waveguide and to absorb waves of the harmonic frequency travelling in the opposite direction, thereby preventing RF waves of the harmonic frequency from being reflected back into the RF source (or, if generated elsewhere in the system, from being transmitted to the RF source).

Alternatively, the RF attenuator is a power divider (or three-port Y splitter or power combiner used in reverse) tuned to absorb the harmonic frequency, wherein one side of the divider/splitter is connected to a load.

Method of Designing a Transmission Waveguide

There is provided a method of designing a transmission waveguide so that a maxima of the second harmonic frequency of the magnetron is not coincident with a component of the magnetron, such as the cathode. More particularly, there is provided a method of adjusting the length of a transmission waveguide to move a maxima of the second harmonic frequency of the magnetron relative to the magnetron cathode.

As discussed earlier, critical parts of the RF source (e.g. in the case of a magnetron, the magnetron cathode) absorb energy of the harmonic frequency of the RF source and will consequently overheat. Repeated overheating of the magnetron cathode leads to early failure and thus reduced magnetron lifespan.

In embodiments, the length of the transmission waveguide is adjusted to move maxima of the (second) harmonic frequency of the magnetron away from the magnetron cathode.

The length of the transmission waveguide is defined as the total length of the waveguide between the RF window of the magnetron and the RF window of the accelerating waveguide as seen by the fundamental mode of an RF wave travelling along the transmission waveguide.

The length of the transmission waveguide can be adjusted in a number of ways.

Preferably, there is provided a transmission waveguide that is optimised in such a way that the most intense electromagnetic field due to RF waves of the second harmonic frequency of the magnetron exists only in areas outside of the magnetron or in parts of the magnetron which can be cooled easily, for example using a cooling system.

Figure 6:
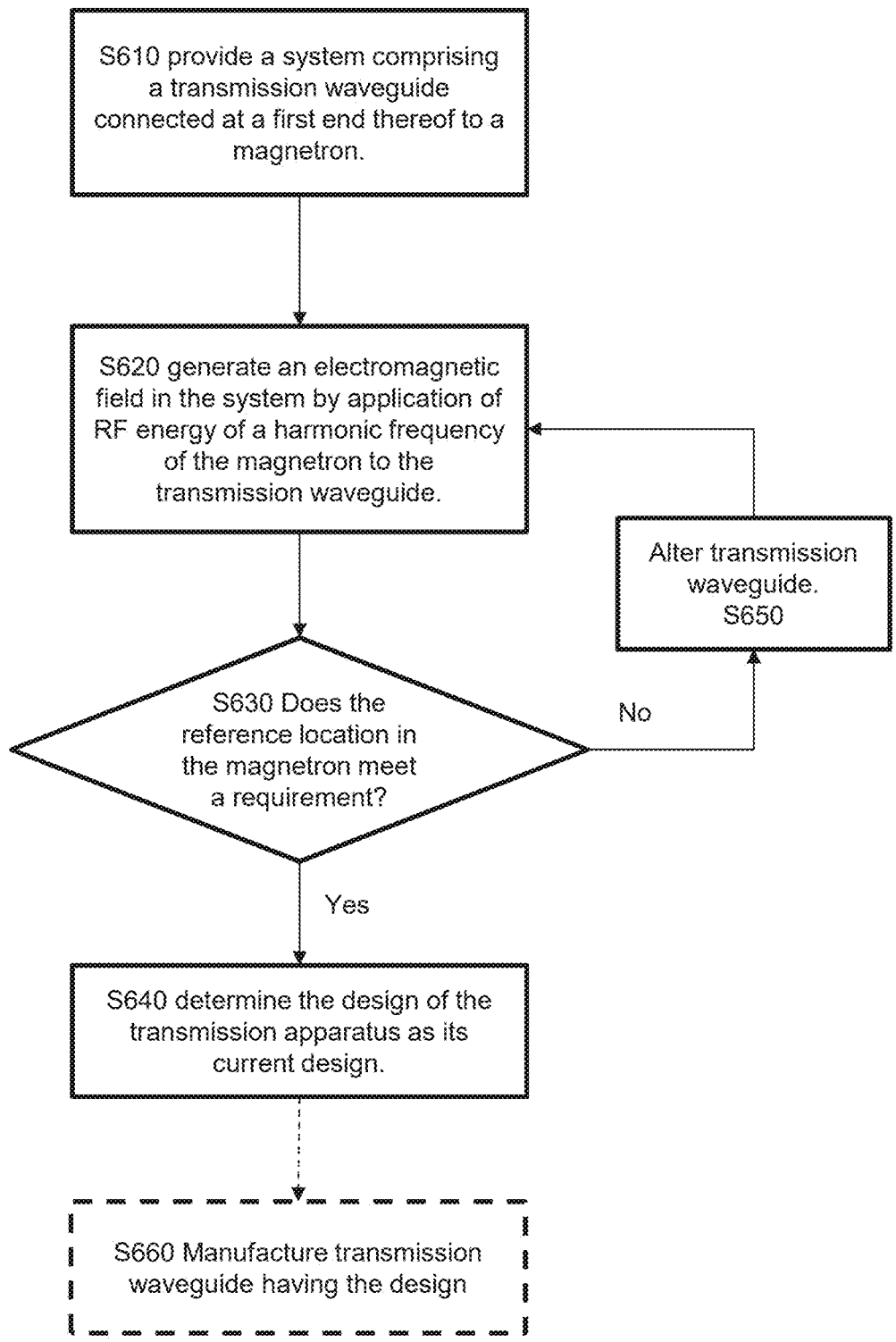
FIG. 6 shows a flow diagram of a method of determining a design of a transmission waveguide in accordance with embodiments.

FIG. 6 illustrates a method of determining a design (e.g. a length) of a transmission waveguide according to embodiments.

In accordance with some embodiments, the method is carried out as a simulation (or emulation), for example on a computer using physics modelling software. In other embodiments, the method is carried out on a physical apparatus including probes or sensors as means of determining properties of the electromagnetic field and/or temperature field in the system.

In the method, a system comprising a transmission waveguide connected at a first end thereof to a magnetron is provided at step S610. The transmission waveguide can be any of the transmission waveguides described in this specification. For example, the transmission waveguide can be of the type described with reference to the prior art or of the type described with reference to embodiments, for example including an RF attenuator configured to attenuate RF waves of the second harmonic frequency of the magnetron.

In some embodiments, the system comprises an accelerating waveguide coupled to a second end of the transmission waveguide. However, it is not essential that the system comprises an accelerating waveguide since a component that is capable of mimicking the effects of an accelerating waveguide can be coupled to the second end of the transmission waveguide. If the method is carried out as a simulation, then boundary conditions may be set at the second end of the transmission waveguide which emulate the presence of an accelerating waveguide.

The length of the transmission waveguide is identified, defined as the total length of the transmission waveguide between the first and second ends thereof. The total length is the path length as seen by the fundamental mode of an RF wave generated by the magnetron travelling in the transmission waveguide from the first end to the second end. In the context of a system, the transmission waveguide includes all of the components acting wholly or partly as a waveguide for RF waves travelling between the RF window of the magnetron and the RF window of the accelerating waveguide.

At step S620 an electromagnetic field is generated in the system by application of RF energy of a harmonic frequency of the magnetron to the transmission waveguide. The harmonic frequency can be any order harmonic, for example the third or fourth harmonic. However, the harmonic frequency is preferably the second harmonic frequency as this has been identified by the inventors as being the frequency most damaging to the magnetron.

If the method is carried out as a simulation, the electromagnetic field is generated by the application of a source of electromagnetic radiation in the system. In this case, the behaviour of the electromagnetic radiation in the system which gives rise to the electromagnetic field is determined by equations governing the properties of the system and the physics determining the propagation of RF waves in the system.

If the method is carried out using a physical apparatus, then the source of the RF waves would need to be the RF source in question in order to replicate the system effects. If the source in question is a magnetron then it is preferable that the magnetron in question is used rather than a frequency generator (which not be able to duplicate the system effects). The experimental setup would require the use of directional power couplers that have been calibrated (or at least had their coupling factors) to the be able to measure frequencies of interest/concern and the system would need to be monitored by a spectrum analyser, frequency counter and suitable power meters in order to understand where power was being deposited in the system. The methodology shown in FIG. 6 would still be applicable to this experimental investigation.

In a simulation, the RF electromagnetic field is based on the physics of RF wave behaviour. This may be approached using commercially available software capable of solving Maxwell's equations in terms of the specialised application of linear accelerators (e.g. a software package that prevents the inclusion of spurious solutions as a result of the boundary conditions). The skilled person knows how to construct such a model depending on the particular software package or calculation method employed and the specification of the magnetron, RF transmission waveguide and accelerator in question. The electromagnetic and/or thermal effects may either be handled directly by the software package or may be added to the simulations by external means via a third party software code.

The approach is the same as that described in FIG. 6, however there are some additions that need to be factored in section S610 and these include a physics model of the relevant aspects and/or behaviour of the RF power source. Alternatively, the nature of the RF output of the RF power source (e.g. the amount of power in one or each of the harmonics generated by the RF power source) are required as an input to the modelling process.

The following two alternative approaches may be used in determining the effect of the harmonics other than the fundamental on the complete RF system:

a) As part of S610, the entire system may be modelled in the time domain coupled with a particle-in-cell PIC solver (for both the unloaded system and loaded system with electron beam in the accelerator). This can be very computationally expensive as medical accelerators tend to have an amount of energy stored within their structures and this constitutes a large Quality (Q) factor which requires a lot computational resource for a time domain solver to converge to an acceptable accuracy. Additionally, it may be necessary to sweep the entire span of potential resonances in order to look for system effects.

b) The RF system components are considered separately as a series of interlinked simulations. In such a scenario a joint eigen mode and PIC solver is employed for the linac to map out the resonant modes of the linac (both unloaded and loaded with electron beam). Once the resonant modes are found, the equivalent input power condition for each of the modes is determined and based on the amount of reflected power back into the system particular harmful modes would be identified for further simulations. The output is then used as an input as boundary power conditions (at the calculated frequencies) into the other RF components in the system including the transmission waveguide in which the simulations are followed throughout the conjoined RF components ending in the RF power source.

The method is not limited to these approaches and, as the skilled person will recognise, other modelling strategies can be employed to determine the amount of power of the harmonic frequency (or frequencies) that interact with the RF power source.

Regardless of the modelling approaches used, the amount of reflected power that interacts with the RF power source may then be used to determine the additional thermal heating that the RF power source component would see during its operation. The resulting temperature of the RF power source component is then used to update the emission characteristics of the RF power source which is then fed back into the RF model to determine the power reflected back to the RF power source. Ultimately this is used to determine the effect on the system and hence the lifetime of the RF power supply. If this is deemed to be detrimental to the system (e.g. by determining that a requirement has not been met as described later) then a continuation of the S630 design loop can be performed in terms of either alteration of the transitional distance (e.g. by alteration of the length of the transmission waveguide) or the addition, modification or moving of an RF attenuator in the transmission waveguide before the simulation is run again to determine whether or not the requirement is met. Said RF attenuator may be any of the RF attenuators arranged to attenuate a harmonic frequency of the RF source described herein.

If the method is performed in a simulation, the electromagnetic field generated by the application of the RF wave in the transmission may be mapped out as a point cloud over the internal volume of the system or over internal surfaces in the system. In some embodiments, the representation of the electromagnetic field in the simulation is a false-colour map, but this disclosure is not limited to such representations and other representations of the simulated electromagnetic field data are also included.

Due to the absorption of the electromagnetic field by parts of the magnetron, the generated electromagnetic field gives rise to a temperature field in the components of the system. In embodiments, the simulation method includes determining the temperature field in the RF power source due to the absorption of the electromagnetic radiation of the harmonic frequency and effects related to this additional electromagnetic field this may have.

At step S630 the method includes determining whether a reference location in the magnetron meets a requirement (e.g. a field requirement). In embodiments, the reference location in the RF power source is any part of the RF power source which can be adversely affected by absorption of these unwanted reflected RF waves. For example, the reference location can be the magnetron cathode or on the surface of the magnetron cathode (if a magnetron is used as an RF power source). The reference location is either a locus of points in the RF source, a surface of the RF source or a single point in the RF source.

Determining whether a reference location in the magnetron meets a requirement includes one or more of:

Determining whether a nearest maxima of the electromagnetic field to the reference location is located above a threshold distance from the reference location. In this case, if the reference location is a locus of points, the distance from the reference location may be a shortest distance from the locus of points to the nearest maxima of the electromagnetic field. Alternatively, the distance may be the distance from the centre of the locus of points to the nearest maxima of the electromagnetic field.

Determining whether a nearest minima of the electromagnetic field to the reference location is located below a threshold distance from the reference location. In this case, if the reference location is a locus of points, the distance from the reference location may be a shortest distance from the locus of points to the nearest minima of the electromagnetic field. Alternatively, the distance may be the distance from the centre of the locus of points to the nearest minima of the electromagnetic field.

Determining whether a maxima of the electromagnetic field is spaced apart from the reference location.

Determining whether a minima of the electromagnetic field is collocated with the reference location.

Determining whether a value of the electromagnetic field at the reference location is below a threshold value.

Determining whether a value of the temperature field at the reference location is below a threshold value.

Determining a change in the emission characteristics of a material as a either a direct or indirect result of the electromagnetic field at the reference location.

Determining the change in performance of generated RF as either a direct or indirect result of the electromagnetic field from dark current and or arcing effects.

Determining the change in performance of the generated RF as either a direct or indirect result of the thermal heating from the electromagnetic field altering or causing undue stress on the RF power source by altering its internal geometry and or causing unwanted AFC changes to the system.

Other determinations of whether the reference location meet the requirement are also possible provided that they perform the function of identifying whether the reference location is likely to be put under thermal stress due to the electromagnetic field in the system or have adverse electromagnetic or emission effects as a result of this additional heating.

When the embodiment includes determining whether a nearest maxima of the electromagnetic field to the reference location is located above a threshold distance from the reference location, if the chosen solution is not to use one of the RF absorber concepts to prevent the presence of the unwanted electromagnetic being reflected back to the RF source, the problem will consist of shifting the point of interaction away from the critical part of the RF source to a less critical one as has been outlined in the designing a transmission waveguide described herein. In this method it is desirable to move the nearest maxima as far from the reference location as possible without causing other maxima to become the (new) nearest maxima to the reference location. Therefore, the threshold distance may be up to one quarter the wavelength of the harmonic frequency. Any movement of the nearest maxima of the electromagnetic field away from the reference location is beneficial. However, it is preferable that the nearest maxima is located at a distance of at exactly one quarter the wavelength or the harmonic frequency of the magnetron from the nearest maxima (i.e. so that a minima of the electromagnetic field is collocated with the reference location). During the process the entire RF power source is checked such that no new detrimental effects are introduced while relocating the reflected electromagnetic field within it. The electromagnetic field causing the issue within the RF source is moved to a less critical part of the structure whereby the lifetime of the RF source may be extended to an acceptable level.

At step S630, if the reference location meets the requirement, the method includes a step S640 of determining the design of the transmission waveguide as its current design. Optionally, at step S660 a transmission waveguide having the final design is manufactured.

Method steps S610-S630 can be used to check whether a transmission waveguide has been manufactured using the method in FIG. 6; the step S630 resulting in a 'yes' output would confirm that the transmission waveguide has the required design.

At step S630, if the reference location does not meet the requirement, the method includes a step S650 of altering the transmission waveguide and repeating steps S620 and S630.

Altering the transmission waveguide can include one or more of:
Altering the length of the transmission waveguide by:
Adding an RF spacer placed in line in the transmission waveguide, for example between two or more sections of the transmission waveguide, or between one section of the transmission waveguide and the magnetron, or between one section of the transmission waveguide and the accelerating waveguide; or
Lengthening or shortening one or more sections or components of the transmission waveguide (i.e. by replacement thereof with longer or shorter sections or components); or
Adding an RF attenuator to the transmission waveguide; or
Modifying an RF attenuator already present in the transmission waveguide; or
Moving an RF attenuator within the transmission waveguide.

The above described replacement or additional components used to alter the length of the transmission waveguide may include any one or more implementations of the RF attenuator described herein. Advantageously, this provides the effect of both reducing the amplitude of the harmonic frequency in the magnetron and moving high intensity fields away from critical components of the RF source.

Optionally, when steps S620 and S630 are repeated after altering the design of the transmission waveguide, the requirement changes from an initial requirement before the design is altered to a modified requirement after the design is altered, wherein the modified requirement is different from the initial requirement. In some embodiments, the modified requirement is dependent on a value (e.g. a measured characteristic of a part of the RF source or a field value in the system) at the reference location before the design of the transmission waveguide was altered.

For example, if the value at the reference location included a first value before the design was altered, then the modified requirement is that the value at the reference location after altering the design is lower than the first value, optionally lower by a threshold amount. The value in this case can be a field value such as a temperature field value or the electromagnetic field value.

Alternatively, if a nearest maxima of the electromagnetic field is a first distance from the reference location before the design is altered, then the modified requirement is that the nearest maxima to the reference location after the design is altered is a greater distance than the first distance, optionally greater by a threshold amount.

If the requirement in any of the above method permutations is met, then the altered design is output as the 'design' at step S640 and optionally a transmission waveguide having the final design is manufactured. If the requirement is not met, the method returns to step S650 and the design is altered again. The design can be altered based on the original design (i.e. returning to the original design and making alterations) or based on the altered design to give rise to an iterative method.

The method can be applied to ensure that a minima of the electromagnetic field is located for example on the magnetron cathode, or that a maxima of the electromagnetic field is located a threshold distance away from the magnetron cathode.

Figure 7A:
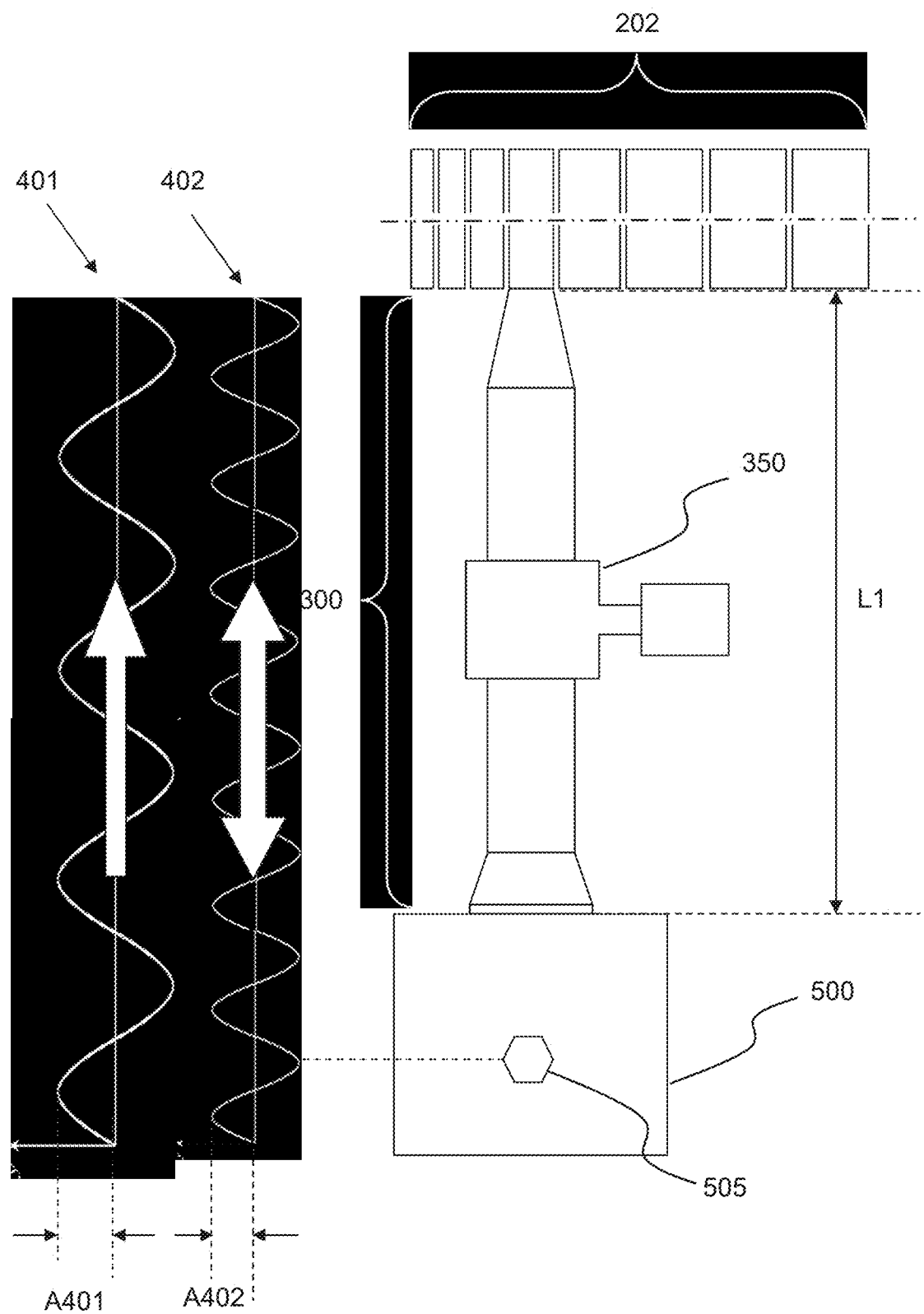
FIG. 7A shows a system including a transmission waveguide connected between a magnetron and an accelerating waveguide in accordance with the prior art, and a schematic of waves of the fundamental and a harmonic frequency of the magnetron in the system.
Figure 7B:
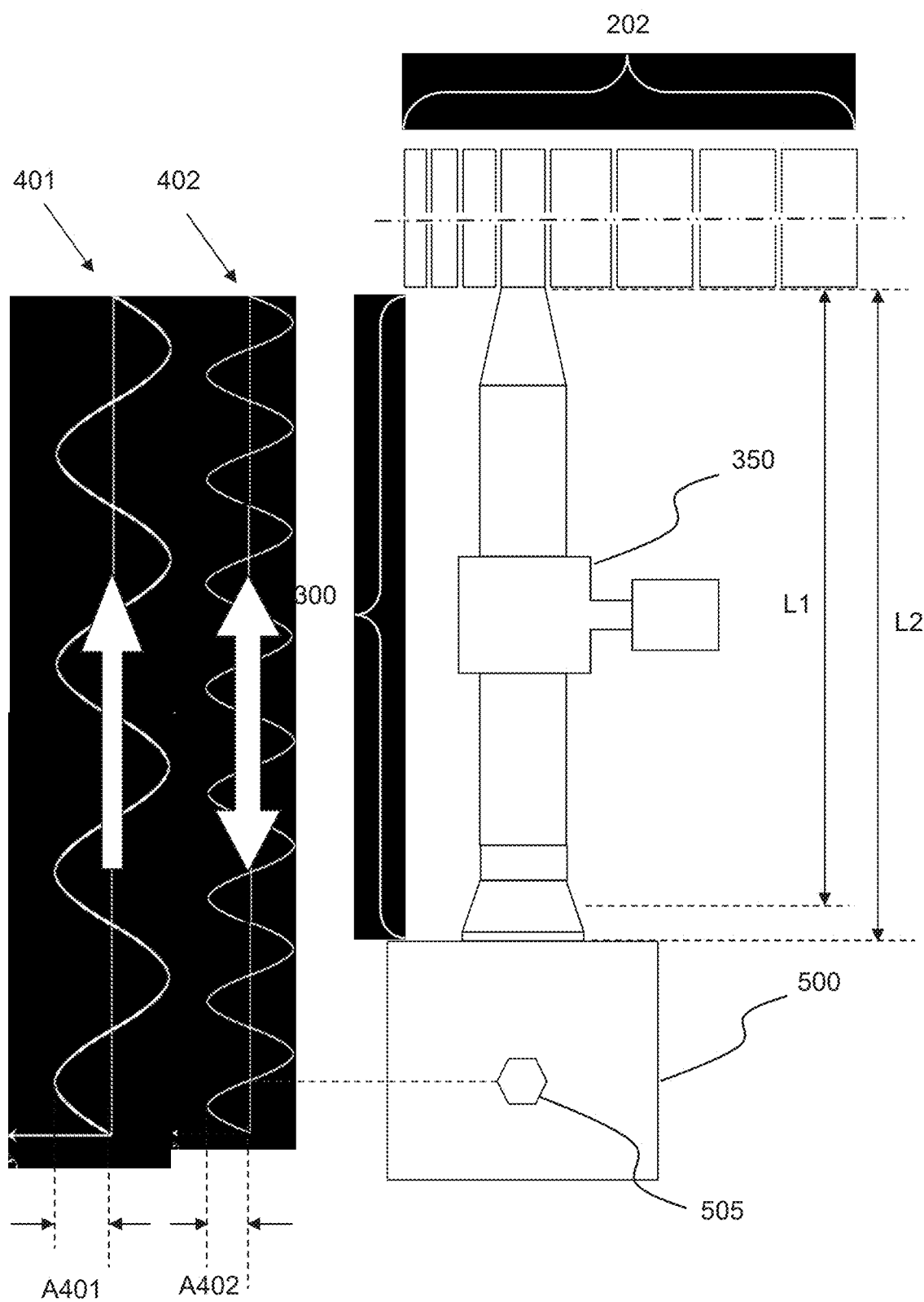
FIG. 7B shows the system of FIG. 7A altered so that the length of the transmission waveguide is increased.

FIGS. 7A and 7B show an example of a transmission waveguide altered so as to move the maxima of a harmonic wave away from a component of the RF source.

FIG. 7A shows a system which the same in all respects to that described with reference to FIG. 4A, but with further detail showing a critical component 505 of the RF source 500 and its position relative to a maxima of the harmonic wave 402. The system may or may not also include any of the RF attenuators described herein in the transmission waveguide.

As can be seen from FIG. 7A, the length L1 of the transmission waveguide 300 has resulted in the colocation of a maxima of the harmonic wave 402 and the critical component 505. This leads to a finding that the above described 'requirement' has not been met because there is a high intensity electromagnetic field due to the harmonic wave 402 at the critical component 505. The above described 'reference location' is collocated with the critical component 505 in this embodiment. The critical component 505 is, for example, the cathode if the RF source is a magnetron.

FIG. 7B shows the same transmission waveguide 300, but altered so that it has a new length L2. The new length L2 results in a finding that the 'requirement' is met because there is a low intensity electromagnetic field at the reference location due to the harmonic wave 402 having a minima collocated with the critical component 505. Since the requirement in this met, L2 is output as the design length of the transmission waveguide 300. A transmission waveguide manufactured having design length L2 would have a longer lifetime than one having a design length L1, because the electromagnetic field at the critical component is lower and thus overheating of the critical component is avoided.

Advantageously, the methods described herein allow the transmission waveguide to be designed such that there is minimum heating of critical parts of the RF source. The inventors have identified that the in the situation of using a magnetron as an RF source the magnetron cathode is particularly susceptible to damage by repeated overheating. Therefore, the reference location in the above methods is preferably in or on the surface of the magnetron cathode.

Furthermore, the inventors have identified that the second harmonic frequency of the magnetron causes the most damage and hence preferably the harmonic frequency referred to in the methods described above is the second harmonic frequency of the magnetron.

Although the above method is described with reference to moving maxima of the electromagnetic field away from the magnetron cathode, it is also possible to perform the same method with the goal of moving maxima of the electromagnetic field away from another part of the magnetron. This may be desirable if, for example, damage to the magnetron occurs in a part of the magnetron other than the magnetron cathode.

Also described herein are the following numbered embodiments:

Embodiment 1. A transmission waveguide for a particle accelerator, the particle accelerator comprising an RF source having a fundamental frequency, wherein the transmission waveguide:
is configured to transmit RF waves of the fundamental frequency; and
comprises an RF attenuator configured to attenuate RF waves of a harmonic frequency of the RF source.

Embodiment 2. The transmission waveguide according to embodiment 1, wherein the transmission waveguide further comprises a circulator configured to operate at the fundamental frequency of the RF source.

Embodiment 3. The transmission waveguide according to embodiment 1 or 2, wherein the RF attenuator is configured to attenuate a greater proportion of RF waves of the harmonic frequency of the magnetron than RF waves of the fundamental frequency of the RF source.

Embodiment 4. The transmission waveguide according to any preceding embodiment, wherein the RF attenuator comprises an RF absorber.

Embodiment 5. The transmission waveguide according to embodiment 4, wherein the RF absorber comprises a coating configured to absorb RF waves of the harmonic frequency of the RF source.

Embodiment 6. The transmission waveguide according to embodiment 4 or 5, wherein the RF attenuator comprises a waveguide section comprising the RF absorber.

Embodiment 7. The transmission waveguide according to any preceding embodiment, wherein the RF attenuator is configured to pass RF waves of the fundamental frequency of the RF source in a first direction.

Embodiment 8. The transmission waveguide according to embodiment 7, wherein the RF attenuator comprises an isolator.

Embodiment 9. The transmission waveguide according to any preceding embodiment, wherein the RF attenuator comprises a low-pass filter configured to pass waves of the fundamental frequency of the RF source and attenuate waves of the harmonic frequency.

Embodiment 10. The transmission waveguide according to embodiment 9, wherein the low-pass filter comprises a waffle-iron filter.

Embodiment 11. The transmission waveguide according to any preceding embodiment, wherein the RF attenuator comprises an RF resonator cavity configured to resonate RF waves at the harmonic frequency of the RF source.

Embodiment 12. The transmission waveguide according to embodiment 11, wherein the RF resonator cavity comprises the RF absorber of embodiment 4 or 5.

Embodiment 13. The transmission waveguide according to any preceding embodiment, wherein the harmonic frequency of the RF source is the second harmonic frequency.

Embodiment 14. A radiation beam generation apparatus comprising:
an RF source;
an accelerating waveguide; and
the transmission waveguide of any preceding embodiment.

Embodiment 15. The radiation beam generation apparatus according to embodiment 14, wherein the RF source is a magnetron.

Embodiment 16. A linac comprising the radiation beam generation apparatus according to embodiment 14 or 15.

Embodiment 17. A radiotherapy device comprising the linac according to embodiment 16

The invention claimed is:

1. A method of determining a design of a transmission waveguide, the method comprising:
providing a system comprising a transmission waveguide connected at a first end thereof to an RF source;
generating an electromagnetic field in the system by application of RF energy of a harmonic frequency of the RF source to the transmission waveguide;
determining whether a reference location in the RF source meets a requirement relating directly or indirectly to the electromagnetic field in the RF source, wherein the reference location is a part of the RF source adversely affected by absorption of the RF energy;
determining the design of the transmission waveguide based on the requirement being met; and
outputting the determined design.

2. The method of claim 1, wherein responsive to the requirement not being met, the method further comprises:
altering the transmission waveguide by one or more of:
adding an RF attenuator to the transmission waveguide;
modifying an RF attenuator in the transmission waveguide;
moving a position of an RF attenuator in the transmission waveguide; or
altering a length of the transmission waveguide;
generating an electromagnetic field in the altered transmission waveguide by application of RF energy of a harmonic frequency capable of detrimentally affecting the RF source to the altered transmission waveguide; and
determining whether the reference location in the RF source meets the requirement.

3. The method of claim 2, further comprising:
repeating the method of claim 2 until the requirement is met.

4. The method of claim 2, wherein the requirement changes from an initial requirement before the transmission waveguide is altered to a modified requirement after the transmission waveguide is altered, and wherein the modified requirement is different from the initial requirement, wherein the modified requirement comprises at least one of: i) a value at the reference location that is lower than a first value determined before altering the transmission waveguide, or ii) a distance from the reference location to a nearest maxima of the electromagnetic field that is greater than a first distance determined before altering the transmission waveguide.

5. The method of claim 4, wherein the modified requirement is dependent on a value at the reference location before altering the transmission waveguide.

6. The method of claim 5, wherein the value is a temperature field value or an electromagnetic field value and/or a value derived either directly or indirectly therefrom having a measurable detrimental effect on an RF performance of the RF source, and/or wherein the value is related to a threshold attribute of at least a part of the RF source.

7. The method of claim 5, wherein a first value at the reference location is determined before the transmission waveguide is altered, and wherein the modified requirement is that a second value at the reference location determined after altering the transmission waveguide is lower than the first value.

8. The method of claim 5, wherein a nearest maxima of the electromagnetic field to the reference location before the transmission waveguide is altered is determined to be a first distance from the reference location, and wherein the modified requirement is that the nearest maxima to the reference location after the transmission waveguide is altered is a greater distance from the reference location than the first distance.

9. The method of claim 2, wherein altering the transmission waveguide comprises:
increasing or decreasing the length of the transmission waveguide by less than a quarter of a wavelength of the harmonic frequency of the RF source.

10. The method of claim 2, wherein altering the transmission waveguide includes adding a spacer or a waveguide section to the transmission waveguide.

11. The method of claim 1, wherein the requirement is an electromagnetic field requirement or a temperature field requirement.

12. The method of claim 1, wherein the requirement is that a nearest maxima of the electromagnetic field to the reference location is located above a threshold distance from the reference location.

13. The method of claim 1, wherein the method is simulated in a computer model.

14. The method of claim 1, wherein the reference location is a locus of points in the RF source.

15. The method of claim 1, wherein the reference location is a single point in the RF source.

16. The method of claim 2, wherein the RF source is a magnetron.

17. The method of claim 16, wherein the reference location is collocated with a part or whole of a cathode of the magnetron.

18. The method of claim 16, wherein the system further comprises:
an accelerating waveguide, wherein the transmission waveguide is connected at a second end thereof to the accelerating waveguide.

19. The method of claim 16, wherein a harmonic frequency of the magnetron is a second harmonic frequency.

20. The method of claim 19, wherein the harmonic frequency has a detrimental effect on the RF source, and wherein the harmonic frequency includes the second harmonic frequency of the magnetron when the magnetron is being used as the RF source.

21. The method of claim 19, wherein the RF attenuator is configured to attenuate a greater proportion of RF waves of the harmonic frequency of the magnetron than RF waves of the harmonic frequency of the RF source.

22. The method of claim 2, wherein the RF attenuator comprises an RF absorber.

23. The method of claim 22, wherein the RF absorber comprises:
a coating configured to absorb RF waves of the harmonic frequency of the RF source.

24. The method of claim 22, wherein the RF attenuator comprises:
a waveguide section comprising the RF absorber.

25. The method of claim 2, wherein the RF attenuator is configured to pass RF waves of the harmonic frequency of the RF source in a first direction.

26. The method of claim 25, wherein the RF attenuator comprises an isolator.

27. The method of claim 2, wherein the RF attenuator comprises:
a low-pass filter configured to pass waves of the harmonic frequency of the RF source and attenuate waves of the harmonic frequency.

28. The method of claim 27, wherein the low-pass filter comprises a waffle-iron filter.

29. The method of claim 2, wherein the RF attenuator comprises:
an RF resonator cavity configured to resonate RF waves at the harmonic frequency of the RF source.

30. The method of claim 29, wherein the RF resonator cavity comprises an RF absorber.

31. A method of fabricating a transmission waveguide, the method comprising:
determining a design of the transmission waveguide; and
fabricating the transmission waveguide having the design,
wherein determining the design includes:
providing a system comprising a transmission waveguide connected at a first end thereof to an RF source;
generating an electromagnetic field in the system by application of RF energy of a harmonic frequency of the RF source to the transmission waveguide;
determining whether a reference location in the RF source meets a requirement relating directly or indirectly to the electromagnetic field in the RF source, wherein the reference location is a part of the RF source adversely affected by absorption of the RF energy; and
determining the design of the transmission waveguide based on the requirement being met.

* * * * *